US006896659B2

(12) United States Patent
Conston et al.

(10) Patent No.: US 6,896,659 B2
(45) Date of Patent: May 24, 2005

(54) METHOD FOR ULTRASOUND TRIGGERED DRUG DELIVERY USING HOLLOW MICROBUBBLES WITH CONTROLLED FRAGILITY

(75) Inventors: Stanley R. Conston, San Carlos, CA (US); Ronald Yamamoto, San Francisco, CA (US); Thomas B. Ottoboni, Belmont, CA (US); E. Glenn Tickner, Watsonville, CA (US)

(73) Assignee: Point Biomedical Corporation, San Carlos, CA (US)

( * ) Notice: Subject to any disclaimer, the term of this patent is extended or adjusted under 35 U.S.C. 154(b) by 220 days.

(21) Appl. No.: 10/028,738

(22) Filed: Oct. 22, 2001

(65) Prior Publication Data

US 2002/0151792 A1 Oct. 17, 2002

Related U.S. Application Data (63) Continuation-in-part of application No. 09/638,162, filed on Aug. 11, 2000, now abandoned, and a continuation-in-part of application No. 09/389,868, filed on Sep. 2, 1999, now abandoned, and a continuation-in-part of application No. 09/245,781, filed on Feb. 5, 1999, now abandoned, which is a continuation-in-part of application No. 09/020,046, filed on Feb. 6, 1998, now abandoned.

(51) Int. Cl.$^7$ ................................................. A61B 8/14
(52) U.S. Cl. ........................................................ 600/458
(58) Field of Search ................................ 600/437–472; 424/9.51, 9.52, 489, 450, 400; 73/625, 626

(56) References Cited

U.S. PATENT DOCUMENTS 5,190,766 A * 3/1993 Ishihara ....................... 424/489
5,558,082 A    9/1996 Spencer
5,580,575 A * 12/1996 Unger et al. ................. 424/450
5,585,112 A * 12/1996 Unger et al. ................. 424/450
5,650,156 A *  7/1997 Grinstaff et al. ............. 424/400
5,944,666 A *  8/1999 Hossack et al. ............. 600/458
6,071,495 A *  6/2000 Unger et al. ................ 424/9.51
6,171,246 B1 *  1/2001 Averkiou et al. ........... 600/458
6,193,951 B1    2/2001 Ottoboni et al.
6,224,544 B1    5/2001 Takada
6,319,204 B1 * 11/2001 Brock-Fisher et al. ...... 600/458
6,340,348 B1 *  1/2002 Krishnan et al. ........... 600/447
2001/0012522 A1  8/2001 Ottoboni et al.
2003/0036697 A1  2/2003 Ottoboni et al.

FOREIGN PATENT DOCUMENTS

| WO | WO98/48783  | 11/1998 |
|----|-------------|---------|
| WO | WO99/39697  | 8/1999  |
| WO | WO00/12062  | 3/2000  |
| WO | WO00/527792 | 10/2000 |
| WO | WO01/12069  | 2/2002  |
| WO | WO01/12071  | 2/2002  |
| WO | WO03/034975 | 5/2003  |

* cited by examiner

Primary Examiner—Ali Imam
(74) Attorney, Agent, or Firm—Ann M. Caviani Pease; Dechert LLP (57) ABSTRACT

A method is provided for site specific delivering therapeutic or diagnostic agents to a region in a fluid-filled cavity, vessel or tissue using an agent-loaded microbubble population. The population has controlled fragility characterized by a uniform wall thickness to diameter ratio which defines the discrete threshold intensity value of ultrasonic power where microbubble rupture occurs in the population. The location of the microbubble population may be monitored by ultrasound to determine its presence at the region prior to application of the ultrasonic power to rupture to microbubbles.

25 Claims, 4 Drawing Sheets

Mean Backscatter AD along Flow Phantom @ MI=1.6

Figure 1. Mean Backscatter AD along Flow Phantom @ MI=1.6

Figure 2. Fragility Slope as a Function of Intensity Showing the Critical MI

Figure 3. Averaged Backscatter AD Decay Measured Over Sequential Frames @ MI = 1.6

Figure 4. Fragility Slope as a Function of MI for an Agent Having a $MI_{crit} = 0.22$ Figure 5. Comparison of microbubbles having an arbitrary wall thickness

METHOD FOR ULTRASOUND TRIGGERED DRUG DELIVERY USING HOLLOW MICROBUBBLES WITH CONTROLLED FRAGILITY

CROSS-REFERENCE TO RELATED APPLICATIONS

This is a continuation-in-part of application Ser. No. 09/638,167, abandoned filed Aug. 11, 2000, of application Ser. No. 09/389,868, abandoned filed Sep. 2, 1999, and of application Ser. No. 09/245,781, abandoned filed Feb. 5, 1999, which in turn is a continuation-in-part of application Ser. No. 09/020,046, abandoned filed Feb. 6, 1998, now abandoned, the disclosures of which are all incorporated by reference herein in their entirety.

FIELD OF INVENTION

The current invention relates to a method of delivering a therapeutic agent to a localized region within a subject using ultrasound to trigger the release of the agent from hollow microbubbles having a specified set of mechanical properties.

BACKGROUND OF THE INVENTION

Ultrasound imaging has a wide application in the field of medical practice. Ultrasonic diagnostics refers to the imaging of a region of the human or animal patient using an ultrasound transducer to generate and receive ultrasound waves. Typically, the transducer is placed on the patient's body over the region to be imaged and high frequency sound waves are generated by the transducer and directed at the region. The transducer receives reflected ultrasonic waves from the region and converts the received waves into electrical signals from which an image is generated. Due to the extremely high acoustic reflectivity of gases, contrast agents comprised of gas bubbles with and without encapsulating shells are used to improve the quality of ultrasound images by highlighting the blood pool and the vascular perfusion of organs within the body.

The use of ultrasound contrast agents serving also as drug carriers has been described for gas-filled liposomes in U.S. Pat. No. 5,580,575. A quantity of liposomes containing drug is administered into the circulatory system of a patient and monitored using ultrasonic energy at diagnostic levels until the presence of the liposomes are detected in the region of interest. Ultrasonic energy is then applied to the region that is sufficient to rupture the liposomes to release drugs locally for therapeutic purposes. The ultrasonic energy is described in U.S. Pat. No. 5,558,082 to be applied by a transducer that simultaneously applies diagnostic and therapeutic ultrasonic waves from therapeutic transducer elements located centrally to the diagnostic transducer elements.

The use of gas-filled microcapsules to control the delivery of drugs to a region of the body has also been described in U.S. Pat. No. 5,190,766 in which the acoustic resonance frequency of the drug carrier is measured in the region in which the drug is to be released and then the region is irradiated with the appropriate sound wave to control the release of drug. Separate ultrasound transducers are described for the imaging and triggering of drug release in the target region.

Exemplary contrast agents include, for example, stabilized microbubbles, sonicated albumin, gas-filled microspheres, gas-filled liposomes, and gas-forming emulsions. A variety of methods have been developed for their manufacture. These methods usually involve spray drying, emulsion, or interfacial polymerization techniques. Typically, the result is a microbubble population having a range of diameters with either a fixed or an arbitrarily variable wall thickness. An ultrasonic contrast agent produced by one methodology, for example, may contain microbubbles where each has a shell wall of the same thickness regardless of its diameter. Alternatively, a different method of production may result in a microbubble population with wall thickness varying even between those microbubbles having the same diameter.

Conceptually, for an ultrasound contrast agent to be used as a carrier for therapeutics, the agent would typically be, through processing, internally loaded with a drug. The treated microbubbles are then injected intravenously and allowed to circulate systemically. An ultrasound signal of sufficient energy to rupture the drug-containing microbubbles is applied to a region where the delivery of the drug is desired. The insonating beam destroys the microbubbles and thus releases its payload.

An ultrasound contrast agent having a fixed or an arbitrarily variable wall thickness may not by optimal as a carrier of therapeutic agent. A microbubble population having an arbitrary wall thickness could result in the drug being released prematurely or not at all. Those with thinner more fragile walls may rupture from hydrostatic pressure before reaching the site. Those with thicker more durable walls may not rupture at all. A microbubble population with a fixed wall thickness would similarly be unsuitable. While the strength of an encapsulated microbubble is a function of the thickness of its wall, it is also a function of its diameter. Thus, a relatively smaller microbubble would show more resistance to hydrostatic and acoustic pressures than would a relatively larger bubble having the same wall thickness.

A drug-containing ultrasound contrast agent having a controlled fragility would therefore represent an improvement to the state of the art. For purposes herein, the term "controlled fragility" is taken to describe a microbubble population having the characteristic of being rupturable only when exposed to acoustic energy equal to or greater than a predetermined intensity. That is, below this acoustic intensity threshold, substantially all the microbubbles remain intact while above the acoustic intensity threshold the microbubbles rupture. While in the unruptured state, bubble agents can still be seen ultrasonically in the larger blood pool so that the sonographer can position and focus the scanner transducer on the region of interest prior to increasing ultrasound intensity to initiate agent rupture and concomitant delivery of drug. Thus, the agent can be turned-on or turned-off by controlling the intensity of the insonating signal.

SUMMARY OF INVENTION

The present invention provides a method of delivering therapeutic or diagnostic agents to a region of interest within a subject comprising the steps of introducing an agent-loaded microbubble population having a controlled fragility into the bloodstream of the subject, directing at the region an insonating beam of ultrasound energy at a power intensity sufficient to induce rupture of the microbubbles and subsequent release of the active agent into the region to achieve therapeutic or diagnostic effect, and maintaining the power intensity until at least a substantial number of microbubbles are ruptured. The microbubble population has a controlled fragility characterized by a uniform wall thickness to diameter ratio that defines a discrete threshold power intensity value of ultrasonic energy where microbubble rupture in the population occurs.

An advantage of the invention is that the microbubbles have specific and predetermined acoustic properties such that the specific ultrasound power intensity required to rupture the microbubbles can be predetermined as a release threshold prior to injection into the subject. In addition, microbubbles can be tailored for specific rupture characteristics to allow use of ultrasound conditions which will not cause rupture except in the desired body region.

The method may also include the step of monitoring the location of the microbubbles by ultrasound or other suitable detection technique to detect their presence at the region of interest.

Particularly preferred microbubbles will have a bi-layered shell having an outer layer of a biologically compatible amphiphilic material and an inner layer of a biodegradable polymer. Preferred threshold conditions for rupture are those at power, frequency, and waveform sufficient to provide a mechanical index from about 0.1 to about 1.9.

DETAILED DESCRIPTION OF INVENTION

The method for ultrasound triggered drug delivery according to the present invention relies upon an ultrasonic contrast agent consisting of a population of drug-carrying microbubbles having a controlled fragility which is derived from a specific and constant relationship between the microbubble shell thickness and its diameter. This relationship requires that, irrespective of diameter, the microbubbles exhibit an equivalent resistance to acoustic and hydrostatic stresses associated with an echographic imaging environment.

Controlled fragility of a microbubble in drug release is an important consideration in localizing drugs with ultrasound. Microbubbles containing drugs should be resistant to rupture and inadvertent drug release by normal physiological pressures or by ultrasound conditions of the beam passing through tissues not at the target region. By normal physiological pressures, it is meant those pressures encountered in vivo including pressures within the heart and arteries, as well as compressive pressures of passing through constrictions such as capillaries. At minimum, in the use of microbubbles within the circulatory system, the microbubbles should be resistant to normal intracardiac pressures. For example, albumin microbubbles filled with air have been reported to "disappear" in significant amounts in the left ventricle (Gottlieb, et al., 1984), potentially causing problems in use as a drug delivery system to regions other than the left ventricle or with drugs with significant cardiotoxicity.

The controlled fragility characteristic of the drug containing microbubble is derived from the provision that the wall thickness of the microbubble is linearly related to its diameter. That is, for a given microbubble population the ratio of wall thickness to diameter for each microbubble within the population is a constant. An ultrasound contrast agent so produced would exhibit essentially an equivalent resistance to the stresses imparted by the hydrostatic and acoustic forces present in the ultrasound imaging environment.

It can be shown mathematically that the strength, that is resistance to a hoop stress, of a thin-walled hollow sphere is a function of the diameter of the sphere and the thickness of its wall. Further, this relationship is linearly proportional with diameter and inversely proportional with thickness. Thus, for a given applied pressure, if the ratio of thickness to diameter is constant, then the hoop stress on the sphere wall remains constant irrespective of diameter.

An ultrasonic contrast agent including a spectrum of microbubbles all having the same wall thickness to diameter ratio would therefore exhibit essentially an equivalent resistance to the stresses imparted by the hydrostatic and acoustic forces present in the ultrasonic imaging environment.

The maximum wall stress in a pressurized sphere has been solved by Timoshenko and Goodier. (Timoshenko, S. and J. N. Goodier; "Theory of Elasticity"; McGraw-Hill Book Company, New York, N.Y.; (1951): 356–359.) The authors find that the hoop stress, $\sigma_\theta$, for an elastic homogeneous material is given by:

$$\sigma_\theta = (P/2)(2a^3 + b^3)/(b^3 - a^3) \qquad (1)$$

where
a is the inner radius,
b is the outer radius, and
P is the pressure difference across the wall.
If we assume that wall thickness, h, is very thin, then equation 1 simplifies to:

$$\sigma_\theta = (P/2)(R+h)/h \qquad (2)$$

where R is the mean radius.
If the wall thickness, h, is thin compared to mean radius, R, that is R>>h, equation 2 can be further simplified:

$$\sigma_\theta = (P/2)(R/h) \qquad (3)$$

Rewriting this expression in terms of the diameter, d, we obtain $$\sigma_\theta = (P/4)(d/h) \qquad (4)$$

The hoop stress for all elastic materials has a limit above which the material will fail. It is a physical constant. Letting this value be identified as sq-max and the corresponding pressure causing the failure identified as Pmax and rewriting equation 4, we obtain:

$$P_{max} = 4\sigma_{\theta-max}(h/d) \qquad (5)$$

Thus, it can be noted from equation 5 that the maximum allowable pressure, Pmax, is also a constant so long as the wall thickness to diameter ratio (h/d) remains constant. It becomes a property of the microspheres. If there were a spectral distribution of bubble diameters but all possessed the same h/d ratio, all microspheres would begin to fail at the same pressure. In contrast, if the h/d ratio varies, then there is a plethora of pressures where the agent begins to fail.

The mechanical index (MI) identified on all modem ultrasound scanners is a measure of the maximal rarefactional (negative) pressure in the propagated ultrasound field. If the MI were increased systematically from a transducer focused on a plethora of microbubbles possessing a constant h/d ratio, there would be no breakage until the rarefactional pressure of $P_{max}$ was reached. The value of MI when this event is achieved is referred to as the critical MI ($MI_{crit}$). Microbubbles continue to break for all values above this value of $MI_{crit}$. However, the rate of destruction increases as the power level rises. If the h/d ratio is not constant, then there is not a clean initiation of agent destruction. Failure begins at near zero MI and the rate of destruction increases thereafter. Thus, there is no critical MI, there is no controlled fragility.

In a preferred method of manufacture, a microbubble population having a constant diameter to wall thickness ratio can be produced by an emulsion solvent evaporation process. First, two solutions are prepared. One is an aqueous solution containing an appropriate surfactant material which may be an amphiphilic biopolymer such as gelatin, collagen, albumin, or globulins. Viscosity enhancers may additionally be included. This becomes the outer continuous phase of the emulsion system. The second is made from the dissolution of a wall-forming polymer in a mixture of two water immiscible organic liquids. One of the organic liquids is a relatively volatile solvent for the polymer and the other is a relatively non-volatile non-solvent for the polymer. The relatively non-volatile non-solvent is typically a C6–C20 hydrocarbon such as decane, undecane, cyclohexane, cyclooctane and the like. The relatively volatile solvent is typically a C5–C7 ester such as isopropyl acetate. Other polymer solvents, methylene chloride for example, may be used so long as they are miscible with the accompanying non-solvent. Typically about three parts of the organic polymer solution having a concentration of about 0.5 to 10 percent of the polymer is added to one part of the aqueous biomaterial solution having a concentration of about 1 to 20 percent of the biomaterial.

The wall forming polymer may be selected for its modulus of elasticity and elongation which define the mechanical properties of the polymer. Preferred polymers useful in the fabrication of drug-carrying microbubble ultrasound contrast agent would be biodegradable polymers such as polycaprolactone, polylactic acid, polylactic-polyglycolic acid copolymers, co-polymers of lactides and lactones such as epsilon-caprolactone, delta valerolactone, polyamides, polyhydroxybutryrates, polydioxanones, poly-beta-aminoketones, polyanhydrides, poly-(ortho)esters, and polyamino acids, such as polyglutamic and polyaspartic acids or esters of same. References on many biodegradable polymers are cited in Langer, et al. (1083) *Macromol. Chem. Phys.* C23, 61–125.

The polymer solution (inner organic phase) is added to the aqueous solution (outer phase) with agitation to form an emulsion. A variety of devices can be used to produce the emulsion, e.g. colloid mills, rotor/stator homogenizers, high pressure homogenizers, and sonicating homogenizers. The emulsification step is carried out until the inner phase droplets are in the desired size spectrum. It is this droplet size that will determine the size of the microbubble.

The emulsion thus produced may optionally be further diluted into a water bath with moderate mixing. Mixing is continued while maintaining a bath temperature appropriate for the relatively volatile solvent to evaporate while the relatively non-volatile non-solvent remains. A typical temperature is in the range of 30°–35° C. As the solvent volatilizes, polymer concentration in the droplet increases to a point where it precipitates in the presence of the less volatile non-solvent. This process forms a film of polymer at the surface of the emulsion droplet. As the process continues, an outer shell wall is formed which encapsulates an inner core of the non-solvent liquid. Once complete, the resulting microcapsules can then be retrieved, washed, and formulated in a buffer system. Subsequent drying, preferably by freeze-drying, removes both the non-solvent organic liquid core and the water to yield air-filled hollow microbubbles.

Use of an amphiphilic biopolymer as a surfactant in the outer continuous phase as described above provides for the option of creating a microbubble having a bi-layered shell. If during processing the biopolymer is rendered insoluble, by chemical crosslinking using an aldehyde, glutaraldehyde for example, the material forms a permanent contiguous outer layer enveloping and adhering to the inner polymer layer. The advantage to this construct is to allow separate tailoring of the inner and outer layers to serve different functions. While the inner layer can be modified to provide the mechanical and acoustic properties optimized to a specific drug delivery application, the outer layer can be independently altered chemically, for example to enhance biocompatibility or to increase circulation half-life. Such chemical modifications may include pegylation, succinylation, or amidation as well as attaching to the surface a targeting moiety for binding to selected tissues.

The free circulation of the microbubbles is important to the effective delivery of drugs to a local region targeted with ultrasound. As very few regions of the body receive 100% of the cardiac output of the heart, only a fraction of the total number of microbubbles injected into the circulatory system will reach target regions such as the liver, a tumor, etc., on the first circulating pass. In order to effectively dose the target region, the microbubbles need to recirculate with sufficient half-life to eventually reach the target after a number of cardiac passes. The smaller the fraction of total cardiac output received by the target tissues, the greater the need for extended half-life of the microbubbles to achieve significant delivery of drug to the target. In the case where the microbubbles are targeted in the tissues with biological agents such as antibodies or by mechanical trapping, half-life of the agent becomes less important as the microbubble will preferentially accumulate at the target tissues.

In the bilayer microbubble, the inner layer permits the modification of the mechanical properties of the shell of the microbubble which are not provided by the outer layer. The mechanical properties of the inner layer may be adjusted to provide varying threshold levels of microbubble rupture with ultrasound conditions such as output power. Moreover, the inner layer may provide a drug carrier and/or drug delivery capacity. For dual purpose use as an ultrasonic contrast agent, the inner layer will typically have a thickness which is no larger than is necessary to meet the minimum mechanical or drug carrying/delivering properties in order to maximize the interior gas volume of the microbubble. Generally, the greater the gas volume within the microbubble the better the echogenic properties.

For use as an ultrasonically triggered drug delivery system, the inner layer wall thickness to diameter ratio can be varied to provide varying thresholds to rupture, allowing a threshold release characteristic to be utilized. In addition, the mechanical properties of the inner layer such as ultimate elongation, modulus, stress at failure and fatigue properties can be tailored by material selection.

Selection of the appropriate mechanical strength of the inner layer allows imaging at conditions which do not necessarily trigger drug release, but drug release may be triggered during imaging by altering the ultrasound characteristics. These characteristics are important for controlling and localizing release, especially as matched to the localization of the threshold ultrasound conditions for drug release.

Any of a variety of therapeutics may be encapsulated in the microbubbles. By therapeutic, as used herein, it is meant an agent having a pharmacological or diagnostic effect on the patient. As used herein, the term therapeutic agent is synonymous with the term drug.

The therapeutic agent could be incorporated into the microbubble agent by a number of techniques. In one method, for example, the drug is dissolved or otherwise incorporated into the organic polymer solution during microbubble fabrication. Alternatively, the drug may be incorporated into the microbubbles through a series of secondary steps where the finished product is reconstituted with a solution containing the drug, the suspended microbubbles are made to flood with the drug containing solution, and the result dried, typically by lyophilization. Finally, the drug may be affixed by chemical means to the surface of the microbubble.

Preferred methods of incorporation produce a drug-carrying microbubble that would, upon rupture with insonation, allow ready desolution of the active agent into the blood or other body fluids as required. Those methods which incorporate the drug into the wall structure of the microbubble or provide attachment to the surface may also be useful. In this case it is envisioned that the mechanical properties of the wall would be such that microbubble rupture would result in ultra-small wall fragments which would then carry drug to the local site.

Microbubbles produced by the general procedures outlined above will be of a size approximate to the emulsion droplets from which they were derived. In such a case, a relationship between the concentration of the wall forming material in the polymer solution, the microbubble diameter, and the wall thickness can be derived.

Defining $v_W$=volume of the microbubble wall, $$v_W = VC/\rho \tag{6}$$

where,

V=volume of the emulsion droplet,

C=mass concentration of wall forming material, and $\rho$=dry density of the wall forming material For d>>h, $$h = v_W/S \tag{7}$$

where S=surface area of the emulsion droplet.

Substituting, $$h = VC/Sr \tag{8}$$

Since for a sphere, $V = \pi d^3/6$ and $S = \pi d^2$, $$h = C(\pi d^3/6)/\rho(\pi d^2) \tag{9}$$

Simplifying, $$h = Cd/6\rho \tag{10}$$

rearranging, $$h/d = C/6\rho \tag{11}$$

Since C and $\rho$ are constants for a given set of process conditions, it follows that h/d is also constant.

Upon review of equation 5 and equation 11, it is evident that a methodology exists that can be used to fashion a microbubble population having a constant wall thickness to diameter ratio and that a microbubble population so constructed possesses a controlled fragility useful as a drug-carrying ultrasonic contrast agent.

Adjustment of the controlled fragility property of a microbubble population produced in a manner described above can be achieved in several ways. By manipulating the initial concentration of the wall-forming material in the inner phase solution of the emulsion system, for example, the ratio of h/d can be adjusted to increase or decrease the acoustic intensity threshold at which the microbubble ruptures. Wall material selection can also be used to modify the ultimate wall strength of the microbubble. Those materials having a higher yield stress property would provide for a less fragile microbubble. Average molecular weight of the material may also be manipulated to modify the controlled fragility characteristic as a lower molecular weight material would generally produce a more fragile wall. Use of additives such as plasticizers may also be considered since such additives typically affect the mechanical properties of the material including yield strength.

The thickness of the microbubble shell will depend in part on the mechanical properties required for the particular drug delivery application and within a given lot would vary in accordance with the ratio h/d. Typically, for populations of drug carrying microbubbles in the size range suitable for vascular applications shell thickness will be in the range from about 25 nm to about 1000 nm.

In many drug delivery applications, it is important that the microbubbles circulate through the capillary network unimpeded. For such instances, microbubble diameter should be in the range of 1 to 10 microns.

The controlled fragility characteristics of a microbubble agent may be predetermined by a number of ways. A simple approach is to place a test agent in a beaker after first examining the suspension for optical density and then insonating the suspension at progressively higher MI settings until a degradation in optical density is observed. This point will identify the critical MI.

Acoustic densitometric (AD) methods can also be used. One technique utilizes a Doppler Flow Phantom. The transducer of a commercial scanner is placed in the water well atop the phantom, oriented downwards, and focused on the flow tube. The suspended microbubble agent is pumped through the phantom at constant flow rate and viewed on the scanner. AD measurements are then made from the images. If there is no agent destruction, the AD reading is constant along the length of the flow-tube, as backscatter remains constant therein. The scanner power level is increased and the process is repeated. At some point, the microbubbles will fail and there will be a decrease in AD readings axially along the phantom. This decrease provides two useful pieces of information. The rate of acoustic degradation axially along the tube identifies the fragility rate (measured in AD/cm) and is a function of the local MI. The intercept value with the y-axis, essentially the AD measurement at the phantom entrance, provides a measure of the peak backscatter of the test agent. The process can be repeated for several power settings and the data collected. Following the tests, the measured fragility slopes can then be plotted as a function of MI. The intercept of the x-axis (MI) provides the critical MI for the test agent.

Another AD method utilizes a clear chamber placed under water. Microbubble agent is contained within the chamber without flow. An ultrasound transducer is submerged and oriented toward the center of the chamber containing the test agent. As the scanner emits pulses of ultrasound, the backscattered data is collected over time. If there is no agent destruction, the backscattered signal remains constant over time. The power level is increased and the process is repeated. Again at some point, the agent will begin to fail.

When this occurs, the backscatter will decrease over time as more and more of the agent is destroyed. The decay time constant is noted and the process continued at a higher power level. When sufficient data are collected, the decay time constants are plotted against MI. Again, the intercept of the regression fit to the data with the x-axis identifies the critical MI, that is the value of MI required to initiate microbubble destruction.

Analytical means may also be employed to establish the fragility characteristics of the agent. Microbubble wall thickness and diameter can be determined directly by Scanning Electron or Transmission Electron Microscopy or indirectly from knowledge of the wall material mass density, the microbubble count, and the size histogram. These results may then be incorporated into the appropriate equations along with the wall material constants to estimate the acoustic and/or hydrostatic pressures necessary to rupture the microbubbles. Finally, in-vivo procedures using an appropriate animal model could be established that would be useful in collaborating the in-vitro and analytical results.

These approaches permit the determination of the critical MI which is the primary manifestation of controlled fragility. If the agent does not exhibit a unique characteristic as identified here, the critical MI will be essentially zero. With such an agent, there is no turn-on and turn-off capability. There is no controlled fragility.

The microbubbles may contain a pharmacological agent or agent-carrying reservoir in the shell or more preferably in the central core. The cores of the microbubbles may contain a physiologically compatible gas such as air or nitrogen. If a gas with low solubility is preferred, a perfluorocarbon may be used. Alternatively, the microbubbles may be filled with carbon dioxide if an application calls for rapid dissolution of the gas upon microbubble rupture.

Typically, the drug-carrying microbubbles will be introduced intravenously by injection, but they also may be injected intra-arterially. The microbubbles may also be injected interstitially or directly into any body cavity.

A useful dosage of the therapeutic agent will be administered and the mode of administration will vary depending upon the age and weight of the subject and upon the particular therapeutic application intended. Typically, the dosage is initiated at a lower level and increased until the desired therapeutic affect is achieved.

Typically, the rupture of drug-carrying microbubbles would be achieved using ultrasound scanning devices and employing transducers commonly utilized in diagnostic contrast imaging. In such instances a single ultrasound transducer would be employed for both imaging and triggering of the microbubbles by focusing the beam upon the target site and alternately operating at low and high power levels as required by the application.

Another option is to utilize a plurality of transducers focused at the region so that the additive wave superposition at the point of convergence creates a local intensity sufficient to rupture the microbubbles. A separate imaging transducer would be used to image the region for treatment.

A specially designed transducer or multiple transducer set may be incorporated into a wearable object to treat a selected region or organ to alleviate the need for manual placement of the transducer and to facilitate concentration of the ultrasound at the target site.

The transducer may also be incorporated into the distal section of a cannula; or be implanted within the body near the target site. In the first case, an intra-vascular ultrasound catheter is used to provide the specific ultrasound energy required to disrupt the microbubbles as they pass the catheter. The use of such a system provides for the treatment of target sites downstream from the catheter and in places that standard ultrasound imaging would be impaired, in the lungs for example.

In the case of an implant, the ultrasound transducer is surgically implanted within the body at or near the target site for treatment. The transducer may be treated by induction means through the body wall such that it is inert at all times except during use. The drug-containing microbubbles are injected into the body intra-vascularly and the transducer energized to rupture the microbubbles at the target site. The method is useful for longer term or chronic treatment.

To monitor the location of the drug-carrying microbubbles, one or several pulses of sound may be used and the machine may be paused between pulses to receive the reflected sonic signals. In the rupturing of microbubbles, a distinct ultrasound pulse is received which can be used to calculate the number of microbubbles releasing drug and the cumulative microbubbles triggered.

The drug-containing microbubbles can be imaged with ultrasound under clinically accepted diagnostic power levels for patient safety. While not required, it is preferred that the microbubbles be rupturable for drug release at threshold power levels below the clinically accepted power levels for diagnosis. Specific matching of ultrasound conditions and microbubble response to such conditions are important factors in achieving such controlled release conditions. Preferred acoustic threshold conditions for rupture are those at a power, frequency, and waveform sufficient to provide a mechanical index from about 0.1 to about 1.9.

The sound energy may be pulsed, but continuous wave ultrasound energy is preferred for maximal triggering of drug release from the microbubbles. If pulsing is employed, sound will preferably be pulsed in echo trained links of at least about 3 wave periods and preferably be pulsed in echo trained links of at least about 5 wave periods at a time.

Either fixed frequency or modulated frequency sound may be used. For example, a high to low pulse with an initial frequency of 10 MHZ of sonic energy may be swept with increasing power from one to five watts/cm$^2$. Focused, frequency modulated, high energy ultrasound may increase the rate of local gas expansion within the microbubbles, rupturing them to provide local delivery of therapeutics.

The types of agents to be released from the microbubble agent may, for example, be cardiovascular drugs (endocardium agents) with short circulatory half-lives that affect the cardiac tissues, vasculature and endothelium to protect and treat the heart from ischemic or reperfusion injury or coronary artery from restenosis (anti-restenosis agent). Drugs which target platelets (anti-platelet agent) and white cells (anti-white cell agent) which may plug the microvasculature of the heart after a heart attack are also useful for local cardiac delivery. Another type of drug useful for local delivery is one for which a local effect is required but where systemic effects of the drug would be detrimental. These are typically drugs with high toxicity, for example, locally administered potent vasodilators which would increase blood flow to hypoxic tissue but if delivered systemically would cause a dangerous drop in blood pressure. Suitable drugs include fibronolytic agents such as tissue plasminogen activator, streptokinase, urokinase, and their derivatives, vasodilators such as verapamil, multifunctional agents such as adenosine, adenosine agonists, adenosine monophosphate, adenosine diphosphate, adenosine triphosphate, and their derivatives, white cell or platelet acting agents such as GPllb/llla antagonists, energy conserving agents such as calcium channel blockers, magnesium and beta blockers, endothelium acting agents such as nitric oxide, nitric oxide donors, nitrates, and their derivatives, free-radical scavenging agents, agents which affect ventricular remodeling such as ACE inhibitors and angiogenic agents, and agents that limit restenosis of coronary arteries after balloon angioplasty or stenting.

In addition to therapeutic agents delivered locally to the heart, the use of vasodilators in the microbubbles will have enhanced diagnostic application. Vasodilators are used in cardiology to assess the coronary blood flow reserve by comparing blood flow in the heart with and without the maximal vasodilation by the pharmacological agent. Coronary blood flow reserve correlates well with patient prognosis since the reserve capacity enables the myocardium to remain viable during a heart attack. Adenosine and other vasodilators are used during interventional cardiology and nuclear imaging to determine coronary reserve. A microbubble agent which contains a vasodilator will be useful in echocardiography to examine the myocardium under normal conditions, and then upon release of the vasodilator by the ultrasound beam conditions to stimulate local vasodilation. The coronary blood flow reserve may be estimated non-invasively using ultrasound imaging by the extent of hyperemia of the myocardium, Doppler regional flow, or by other well known methods of characterizing the ultrasound imaging data.

The following examples are provided by way of illustration but are not intended to limit the invention in any way.

EXAMPLE 1

Preparation of Polylactide Microbubbles having a Constant Wall Thickness to Diameter Ratio A 6% aqueous solution was prepared from a 25% solution of USP grade human serum albumin by dilution with deionized water. The pH of the solution was adjusted to 4 using 1M HCl. Separately, 0.41 gm poly d,l-lactide and 5.63 gm cyclooctane were dissolved in 37.5 gm isopropyl acetate. The organic solution was then slowly incorporated into 25 gm of the prepared albumin solution with mild stirring while the mixture was maintained at 30° C. The resulting coarse o-w emulsion was then circulated through a stainless steel sintered metal filter element having a nominal pore size of 7 microns. Recirculation of the emulsion was continued for 8 minutes. The emulsion was added with stirring to 350 ml deionized water maintained at 30° C. and containing 1.0 ml of 25% glutaradehyde. During the addition, the pH of the bath was monitored and adjusted as necessary with 1N NaOH to insure that it remained between 7 and 8. Low sheer mixing was continued for approximately 2½ hours until the isopropyl acetate had substantially volatilized. Poloxamer 188 in the amount of 0.75 gm was dissolved into the bath. The resulting microbubbles were retrieved by centrifugation and washed two times in an aqueous solution of 0.25% poloxamer 188. The washed microbubble suspension was then formulated in a glycine/polyethylene glycol solution and lyophilized. The resulting dry white cake was reconstituted with deionized water and examined under the microscope to reveal spherical discrete microbubbles.

EXAMPLE 2

In-Vitro Method for Establishing Acoustic Fragility Threshold

A Hewlett Packard 5500 ultrasound scanner was used for this study in conjunction with an ATS Laboratories, Model 524 Doppler Flow Phantom. The S4 transducer was positioned vertically downward and oriented along the centerline of the 6 mm diameter flow tube within the phantom. The tip of the transducer was placed in the water well above the flow tube. The flow tube appeared as a constant diameter tube (dark interior) in the sector of the scan. The scanner was set in the harmonic mode (1.8/3.6 MHz) with a beam width of approximately 4 cm at the 4 cm depth of the tube centerline below the transducer. A peristaltic pump delivered liquid containing test agent from a 500 ml beaker placed on a magnetic mixer through the phantom and into a discharge container. This fluid was not recirculated. The fluid was stirred constantly in the beaker throughout the test.

Microbubble agent prepared in accordance with the procedures in Example 1 was placed in the beaker, thoroughly mixed with degassed water and pumped through the phantom with a mean velocity of almost 1 cm per second. Flow velocity was maintained constant throughout the test. Axial positions were marked on the scanner monitor and measured from the proximal end of the flow tube along the centerline using the caliper function of the system. A circular (11×11) region of interest (ROI) was selected for the study and used exclusively throughout. The interval was set at 200 ms for any acoustic densitometric (AD) measurement made. Power levels could be varied and local AD measurement made for each power setting and each location. The highest mechanical index (MI) that the system was capable of producing with this setup was 1.6. The system provides 60 reading at 200 ms intervals. The average reading was used for each local reading.

Figure 1:
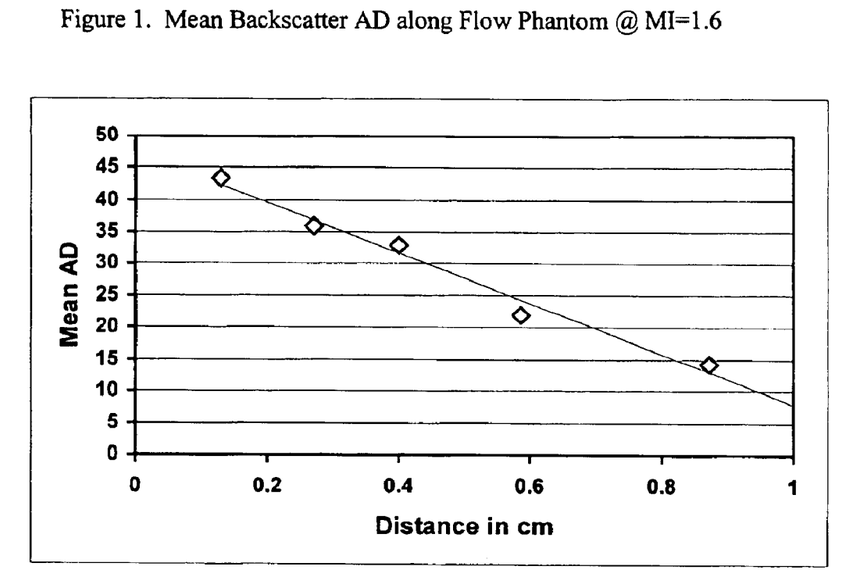
FIG. 1 is a plot of acoustic densitometry measured along the length of the flow phantom described in Example 1.
Figure 2:
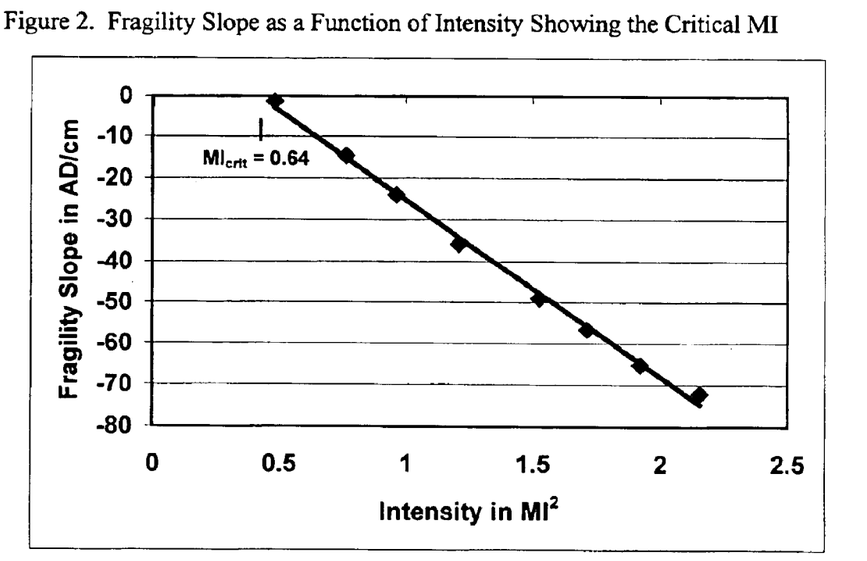
FIG. 2 is a plot of fragility slope verses signal intensity described in the same experiment.

Using the experimental set-up with the HP 5500 and Doppler Flow Phantom as detailed above, an experiment was performed to determine the fragility threshold of the test agent. If the agent does not rupture, the AD reading is constant along the flow phantom. If the agent does rupture, there is a decrease in AD reading along the flow phantom, and there is a slope associated with this decease. This is shown in FIG. 1 for measurements made at an MI of 1.6. A linear regression fit to the data permits the determination of the fragility slope. The fragility slope can then be determined at various MIs when the data is plotted against the square of MI as seen in FIG. 2. The resulting graph permits a determination of where agent begins to fail, i.e., the slope becomes zero. The value of the MI at this point is the critical MI ($MI_{crit}$). Examination of these results reveals that when the mechanical index exceeds 0.64 ($MI_{crit}$=0.64), the agent ruptures. A value below $MI_{crit}$ results in the agent remaining intact.

EXAMPLE 3

Method for Establishing Acoustic Fragility Threshold Using the Decay Method

A Hewlett Packard 5500 ultrasonic scanner was utilized for this study in conjunction with an ATS Laboratories, Model 524 Doppler Flow Phantom. An S4 ultrasound transducer was positioned vertically downward and orthogonal to the center-line of a 12 mm diameter flow tube within the phantom. The tip of the transducer was placed in the water well of the flow phantom. The flow tube appeared with a dark, circular cross-section in the sector of the scan when bubbles were not present and a bright white, solid circle when bubbles were present in the sector scan. The scanner was set in the 2D Harmonic mode (1.8/3.6 MHz) with a beam width of approximately 3 cm at an 8 cm depth from the top of the flow tube. A peristaltic pump delivered water containing test agent from a 1 liter beaker placed on a magnetic mixer through the flow phantom and into a discharge container. This fluid was not recirculated and stirred constantly throughout the test to maintain the suspension uniform.

Microbubble agent prepared in accordance with the procedures in Example 1 was placed in the beaker with thoroughly degassed water and pumped through the phantom. The scanner was placed in the Freeze mode (does not emit excitation signals) and a new batch of test agent pumped into the test section. An 11×11 circular region of interest (ROI) was established at the top center of the flow as seen on the sector scan and the interval was set at 200 ms (0.2 sec between scans). When ready, the scanner was unfrozen and samples collected. Between 12 and 15 scans were collected and the average of these utilized in the data analysis for each power level investigated. An example of one such decay curve in shown in FIG. 3.

Figure 3:
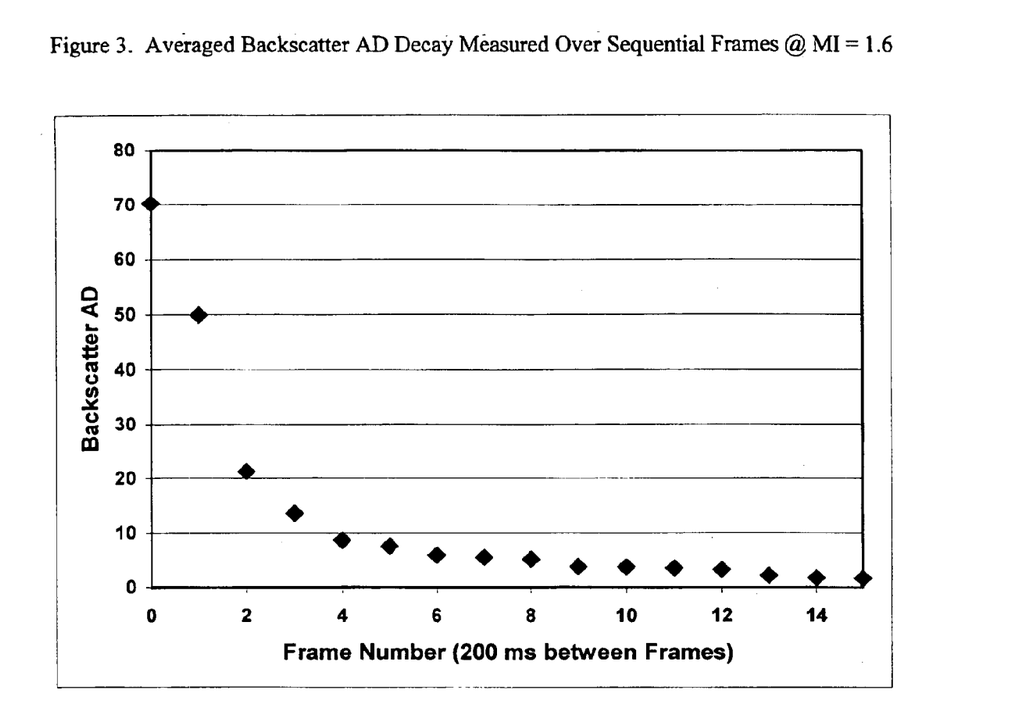
FIG. 3 is a plot of acoustic densitometry decay curve measured according to Example 3.
Figure 4:
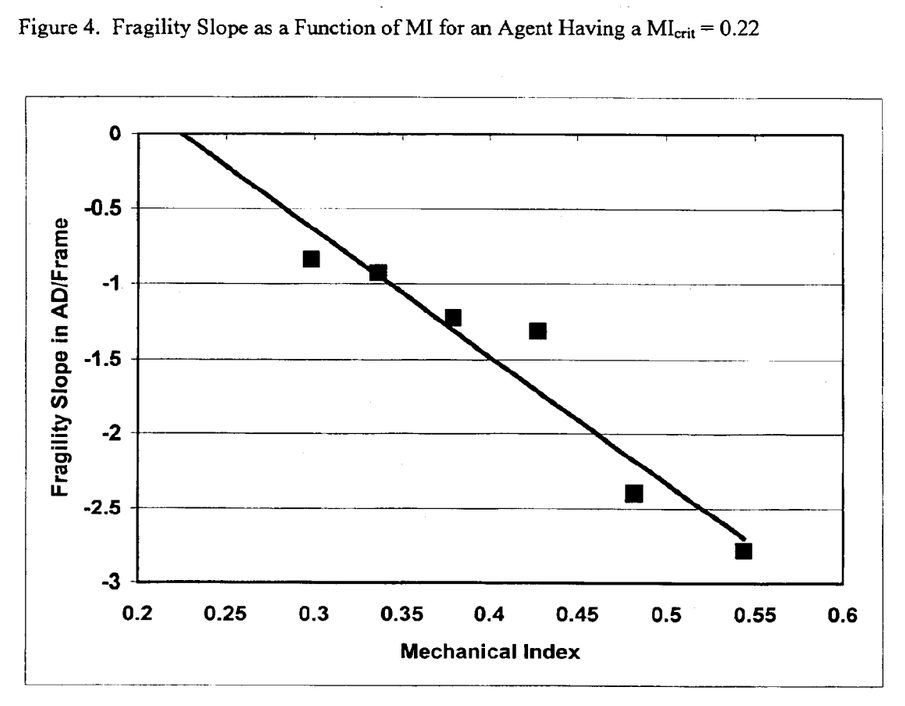
FIG. 4 is a plot of fragility slope v. mechanical index as described in Example 3.

For very low power levels, the backscatter did not decay, but would continue at the same level over all evaluation frames. This means that the agent was not breaking. Therefore, backscatter remained constant over time. The power level was step-wise increased until a decay curve was measured up to a maximum MI of 1.6. The first three points of the decay curve were fit with a linear regression line, which established both (1) the peak backscatter and 2) the decay slope. The peak backscatter is a measure of the backscatter potential of the agent and is dosage dependent. The slope, called fragility slope herein, is a measure of the agent fragility. This slope was found to be proportional to MI. The fragility slope can be plotted against MI. Extrapolation of the data to a zero fragility slope identifies the acoustic fragility threshold or the critical MI. A graph of the fragility slope as a function of MI for the agent is shown in FIG. 4. From the plot the critical MI is determined to be 0.22.

EXAMPLE 4

Comparison of the Fragility Threshold of Microbubble Agent hHaving Different Wall Thickness to Diameter Ratios A family of five agents was prepared in accordance with the procedures described in Example 1. Each agent was fabricated in identical fashion except that the concentration of the polylactide polymer in the organic solution was varied for each run. Each agent would thus be provided with a different wall thickness to diameter ratio. The agents were then tested according to the procedures described in Example 3. From the data, the critical MI for each was determined. The results are presented in Table 1. The results show that the thicker walled microbubbles require more power to rupture than the thinner walled agent. Thus, it is clearly demonstrated that the fragility threshold, or critical MI of the microbubble can be controlled by the construction of the capsule. Further, the fragility of the drug carrying ultrasound contrast agent may be tailored to rupture within the range of diagnostic ultrasound power levels.

TABLE 1

Comparison of Critical MI with Wall-to-Diameter Ratio

| Estimated Wall to Diameter Ratio | Critical MI |
|---|---|
| .016 | .22 |
| .024 | .29 |
| .032 | .34 |
| .041 | .41 |
| .049 | .52 |

EXAMPLE 5

Dye Loading of Microbubbles having Controlled Fragility

To test an agent-carrying ultrasound microbubble population having controlled fragility, a population with a polylactide wall was first prepared in a manner described in Example 1. The resulting lyophilized cake which was prepared in a 10 ml serum vial was removed and then placed into a 50 ml centrifuge tube. Enough isopropyl alcohol was added to cover the cake. The microbubbles quickly became flooded with the isopropyl alcohol. After 30 seconds, a 0.25% w/w aqueous poloxamer 188 solution was added to fill the tube. After centrifuging, supernatant was removed and another rinse performed. A saturated, filtered solution of rhodamine B dye was added to the microparticles and allowed to soak overnight. Under the microscope, the microparticles appeared filled with dye solution. Four ml of a dye saturated poloxamer 188 solution was combined with the approximately 2 ml of the microcapsule suspension. The resulting mixture was divided equally into two 10 ml serum vials and then lyophilized. Both vials were purged with perfluorobutane gas by five pump-down purge cycles with a vacuum pump. Microscopic inspection revealed that roughly half the microbubbles contained gas. The microbubbles were then rinsed 4 times with 20 ml portions of 0.25% poloxamer solution on a vacuum filter. The microbubbles were placed in a cuvette, centrifuged, and an initial spectra was taken. The cuvette was sonicated in an ultrasonic bath, centrifuged, and another spectra taken.

| | |
|---|---|
| Initial Absorbance (553–800 nm): | 1.164 |
| Absorbance after sonication (553–800 nm): | 1.86 |

The higher absorption after sonication indicates that encapsulated dye was released upon insonation of the microbubbles.

EXAMPLE 6

Dye Loading of Polycaprolactone Microbubbles having a Controlled Fragility

Microbubbles were prepared in accordance with the methodology described in Example 1 except that polycaprolactone polymer was used in lieu of polylactide and paraffin in the amount equal to 20% of the polymer was added to the organic phase. The lyophilized cake from one of the prepared vials was placed into a 50 ml centrifuge tube, covered with methanol and allowed to soak for 30 seconds. The tube was then filled with an aqueous solution of 0.25% (w/w) poloxamer 188, gently mixed, and centrifuged in order to precipitate the now fluid-filled microbubbles. The supernatant was removed and the tubes were again filled with poloxamer solution. The fluid-filled microbubbles were resuspended by vortexing and again centrifuged. After removing the supernatant solution, 2 ml of a saturated, filtered solution of brilliant blue G dye in 0.25% poloxamer 188 was added. The fluid-filled microbubbles were allowed to soak for approximately 72 hours. Microscopic examination revealed 90–95% of the fluid-filled microbubbles to be filled with dye solution. A 4 ml sample of a lyophilization excipient was prepared, added to the microbubble suspension, and mixed thoroughly. Two 10 ml serum vials were filled with 3 ml each of the prepared mixture and then lyophilized. Both vials and a portion of deionized water were purged with perfluorobutane for 10 minutes. The vials were then reconstituted with perfluorobutane purged deionized water and rinsed with two 40 ml portions of 0.25% poloxamer 188 on a vacuum filter. The resulting microbubble suspension was split into two 3 ml portions. One portion was sonicated in an ultrasonic bath to rupture the bubbles. Both portions were diluted 1/10 with poloxamer solution and placed into cuvettes. The cuvettes were centrifuged and a visible spectra was taken.

| | |
|---|---|
| Absorbance of Unsonicated sample (605 nm–800 nm): | 0.136 |
| Absorbance of Sonicated Sample: | 0.193 |

The higher absorption after sonication indicates that encapsulated dye was released upon insonation of the microbubbles.

EXAMPLE 7

Figure 5:
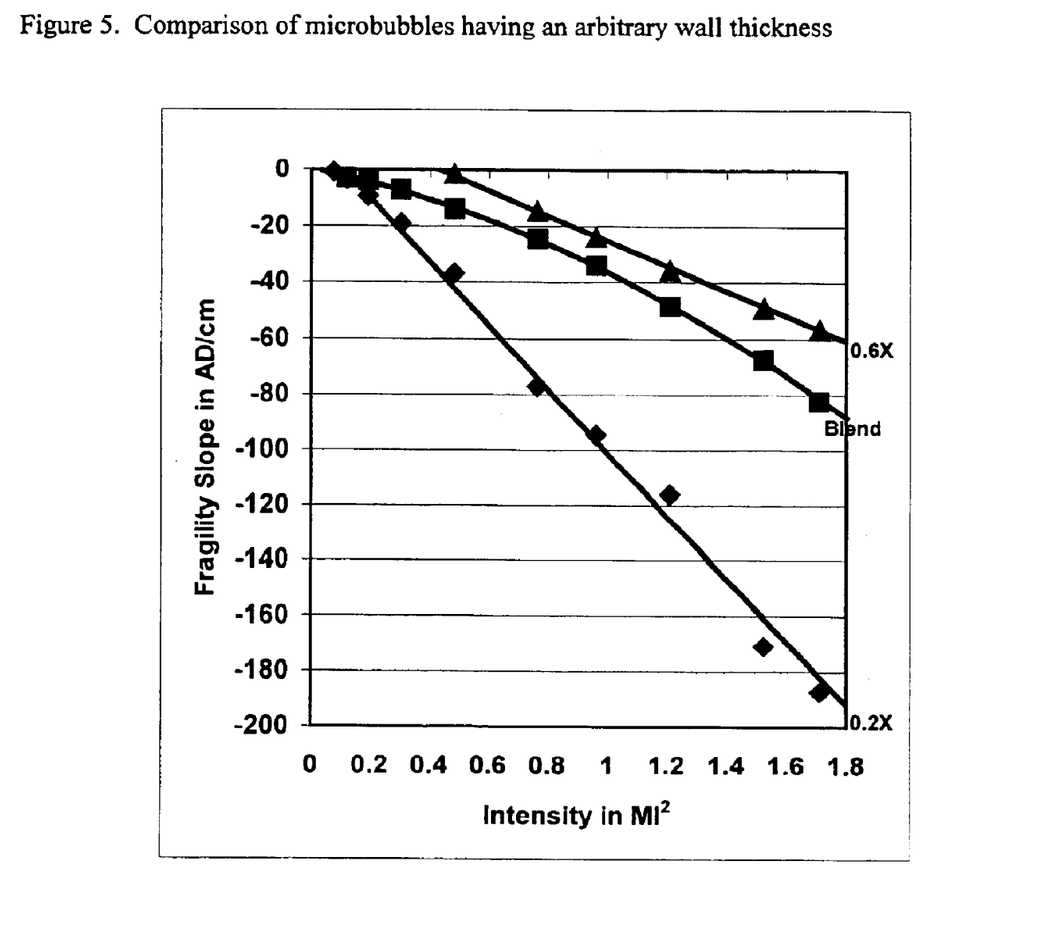
FIG. 5 is a plot of fragility slope v. intensity described in Example 7.

Comparison of Acoustic Response of Microbubbles having Controlled Fragility with Microbubbles having an Arbitrary Wall Thickness In a comparative study, microbubble agent having an arbitrary wall thickness was tested along with two agents exhibiting controlled fragility. The agent having an arbitrary wall thickness was represented by a mixture of several microbubble populations each prepared by means similar to Example 1 but differing in their wall thickness to diameter ratio. This was achieved by varying the concentration of wall forming material for each prepared batch included in the mixture. All other parameters remained the same, including wall material, mean diameter, and spectral size distribution. The Doppler Flow Phantom and the HP 5500 Scanner were employed for this study according to the procedures described in Example 2. Results are shown in FIG. 5.

Three plots are shown on the graph. Two of the plots are results taken from microbubble agents having constant wall thickness to diameter ratios, one representing a relatively durable microbubble population (identified as "0.6x") and one of a relatively fragile population (identified as "0.2x"). The third plot, identified as "blend", are the results derived from the microbubble agent having a variable wall thickness to diameter ratio and hence having an arbitrary wall thickness.

Upon evaluation of the results of the two agents having constant h/d, it is evident that there is a good linear fit to the data even up the point of intercept with the x-axis. This relationship is typical for agents with constant h/d. The critical MI of an agent is determined by identifying the x-intercept. Using linear regression techniques, the critical MI for the 0.2x and 0.6x microbubble agents are calculated to be 0.36 and 0.64, respectively. Note that the 0.6x agent has a higher critical MI than does the 0.2x microbubble agent. This is an expected result since the 0.6x agent has a greater h/d value and thus is the more durable of the two.

By contrast, the data points taken from the agent having the variable h/d displays have neither a linear relationship nor a clearly defined critical MI. The results demonstrate that a microbubble agent having a variable h/d, or synonymously an arbitrary wall thickness, begins to fail almost immediately as those microbubbles in the blend having the thinnest walls would begin to rupture almost immediately. As signal intensity is increased a higher percentage of the agents become involved in the rupture process. Thus, the blended data exhibits a curvilinear relationship indicating the continuous failure of the new material as power is increased. The result is a microbubble agent with no critical MI and hence no controlled fragility.

What is claimed is:

1. A method of site-specific delivery of a therapeutic agent or a diagnostic agent to a region of interest within a fluid-filled cavity, vessel, or fluid perfused tissue by ultrasound comprising the steps of:
   a. introducing an agent-loaded microbubble population into said region of interest, said microbubble population having a controlled fragility characterized by a wall thickness to diameter ratio that defines a threshold power intensity value of ultrasonic energy where microbubble rupture occurs in the population,
   b. applying an ultrasonic signal to the region of interest at a power intensity sufficient to induce microbubble rupture,
   c. maintaining said power intensity until at least a substantial number of microbubbles are ruptured.

2. A method according to claim 1 comprising, prior to said step (b) the step of monitoring the location of said microbubbles within said cavity, vessel or tissue to detect the presence of said microbubbles at said region of interest.

3. A method according to claim 2, wherein said location of said microbubbles is monitored by applying an ultrasonic signal to the region of interest at a power intensity below a threshold power intensity value where microbubble rupture occurs.

4. A method according to claim 1, wherein said microbubble population is comprised of microbubbles having diameters within the range of about 1 to about 10 microns.

5. A method according to claim 1, wherein said microbubble population is comprised of microbubbles having an outer shell comprising an outer layer of biologically compatible amphiphilic material and an inner layer of a biodegradable polymer.

6. A method according to claim 5, wherein said amphiphilic material comprises a protein.

7. A method according to claim 6, wherein said protein comprises collagen, gelatin, albumin, or globulin.

8. A method according to claim 5, wherein said biodegradable polymer comprises polycaprolactone, polylactide, polyglycolide, polyhydroxyvalerate, polyhydroxybutyrate, or copolymers thereof.

9. A method according to claim 1 wherein said region of interest is a heart.

10. A method according to claim 1 wherein said region of interest is a kidney.

11. A method according to claim 1 wherein said region of interest is a liver.

12. A method according to claim 1 wherein said threshold intensity of ultrasonic power where microbubble rupture occurs is sufficient to provide a mechanical index between 0.1 and 1.9.

13. A method according to claim 1 wherein said ultrasonic power is produced by a plurality of transducers focused at said region whereby the intensity and wave superimposition at the point of convergence if the emitted ultrasonic beams is sufficient to rupture the microbubbles.

14. A method according to claim 1 further comprising monitoring the release of said therapeutic or diagnostic agent from the microbubbles to determine rate of release and cumulative dosage released by ultrasonically monitoring microbubble rupture.

15. A method according to claim 1 wherein said ultrasonic power is produced by a transducer embodied within the distal portion of a cannula to disrupt said microbubbles as they flow to said region.

16. A method according to claim 1 wherein said ultrasonic power is produced by a transducer near said region.

17. A method according to claim 1 wherein said ultrasonic power is produced by a transducer affixed to an external, wearable object affixed near said region of interest.

18. A method according to claim 1 wherein said therapeutic agent is a drug to limit ischemic injury to a heart.

19. A method according to claim 1 wherein said therapeutic agent is a drug to limit reperfusion injury to a heart.

20. A method according to claim 1 wherein said therapeutic agent is a drug to limit restenosis of a coronary artery.

21. A method according to claim 1 wherein said therapeutic agent is a drug that comprises a fibrinolytic agent, vasodilator, calcium channel blocker, angiogenesis agent, anti-platelet agent, anti-white cell agent, endocardium acting agent, free radical scavenging agent, or anti-restenosis agent.

22. A method according to claim 21 wherein said drug comprises adenosine, adenosine monophosphate, adenosine diphosphate, adenosine triphosphate or chemical derivatives of adenosine.

23. A method according to any one of claims 1–4 and 9–22 wherein said microbubble population is comprised of microbubbles having an outer shell consisting of a single layer of a biodegradable polymer.

24. A method of claim 23, wherein said biodegradable polymer comprises polycaprolactione, polylactide, polyglycolide, polyhydroxyvalerate, polyhydroxybutyrate, or copolymers thereof.

25. A method of claim 24, wherein said biodegradable polymer is polylactide.

* * * * *